United States Patent [19]
Kossovsky et al.

[11] Patent Number: 5,464,634
[45] Date of Patent: * Nov. 7, 1995

[54] RED BLOOD CELL SURROGATE

[75] Inventors: Nir Kossovsky; Andrew E. Gelman; H. James Hnatyszyn, all of Los Angeles, Calif.

[73] Assignee: The Regents of the University of California, Oakland, Calif.

[*] Notice: The portion of the term of this patent subsequent to Apr. 26, 2011, has been disclaimed.

[21] Appl. No.: 232,756

[22] Filed: Apr. 25, 1994

Related U.S. Application Data

[63] Continuation-in-part of Ser. No. 29,773, Mar. 3, 1993, Pat. No. 5,306,508, which is a continuation-in-part of Ser. No. 199, Jan. 4, 1993, Pat. No. 5,334,394, which is a continuation-in-part of Ser. No. 690,601, Apr. 24, 1991, Pat. No. 5,178,882, which is a continuation-in-part of Ser. No. 542,255, Jun. 22, 1990, Pat. No. 5,219,577.

[51] Int. Cl.$^6$ ............... A61K 9/16; A61K 9/18; A61K 38/42
[52] U.S. Cl. ............ 424/493; 424/490; 424/491; 424/494; 424/498; 424/450; 514/832
[58] Field of Search ............ 424/493, 494, 424/490, 498, 491, 450; 514/832

[56] References Cited

U.S. PATENT DOCUMENTS 5,306,508  4/1994  Kossovsky et al. ............ 424/493

OTHER PUBLICATIONS

Loo et al., "Alkaloid Formation in Ergot Sclerotia," *Science*, vol. 121, Mar. 1955, pp. 367–369.

Lewis, R. W., "Artificial Inoculation of Rye with Ergot. A Susceptible Rye and the Control of Ergot Beetles," *J. Am. Pharm. Assoc.*, Dec. 1948, pp. 511–512.

von Recum, A. F., "Ceramics," *Handbook of Biomaterials Evaluation*, 1986, pp. 38–54.

*Primary Examiner*—Thurman K. Page
*Assistant Examiner*—James M. Spear
*Attorney, Agent, or Firm*—Poms, Smith, Lande & Rose

[57] ABSTRACT

A red blood cell surrogate which is composed of a nanocrystalline core particle to which an oxygen carrier such as hemoglobin is bound. An oxygen carrier anchor coating is provided between the nanocrystalline core particle and the oxygen carrier in order to provide binding of the oxygen carrier to the nanocrystalline core particle without denaturing the oxygen carrier or otherwise destroying its oxygen carrying capacity. The nanocrystalline core particle with the oxygen carrier bound thereto is coated with a layer of lipid and then an outer layer of a sugar or allosteric effector is applied.

29 Claims, No Drawings

RED BLOOD CELL SURROGATE

This is a continuation-in-part of application Ser. No. 08/029,773 which was filed on Mar. 3, 1993, now U.S. Pat. No. 5,306,508, which is a continuation-in-part of application Ser. No. 08/000,199 which was filed on Jan. 4, 1993, now U.S. Pat. No. 5,334,394, which is a continuation-in-part of application Ser. No. 07/690,601, now U.S. Pat. No. 5,178,882, which is a continuation-in-part of application Ser. No. 07/542,255, which was filed on Jun. 22, 1990, now U.S. Pat. No. 5,219,577.

BACKGROUND OF THE INVENTION

1. Field of the Invention

The present invention relates generally to red blood cells and the development of compounds which can be used to replace or supplement red blood cells. More particularly, the present invention relates to synthetic compounds which have the same oxygen transport capabilities as red blood cells and can be used in vivo and in vitro as a red blood cell surrogate.

2. Description of Related Art

There has been, and continued to be, a great deal of interest in developing suitable blood substitutes. One avenue of investigation involves the use of free hemoglobin solutions. However, free monomeric and polymeric as well as cross-linked hemoglobin solutions exhibit osmolarities which are much greater than normal blood. The high osmolarity tends to produce complications of vascular volume and perfusion pressures. Another problem is that unmodified hemoglobin is freely filtered at the glomerulus and is nephrotoxic.

The use of free hemoglobin in a blood substitute is further complicated by contaminants which may be present in the hemoglobin source or which may be introduced during the manufacturing process. Endotoxins and phospholipids are typical examples of contaminants which may be problematic in deploying hemoglobin solutions as blood substitutes. In addition, heterogenous sources of hemoglobin have been shown to produce marked antibody titers in rats. Also, immunogenic complications have also been reported in human trials.

Another approach to blood substitutes involves the use of perfluorocarbons. These blood substitutes typically contain from 10–20% perfluorocarbon by weight and contain particle sizes of approximately 150 nm. The perfluorocarbon type blood substitutes have been reported to have adequate oxygen delivery capacity. However, perfluorocarbons exhibit a linear oxygen dissociation curve which is not desirable for optimum oxygen transport. In addition, perfluorocarbons have several clinical complications. Perfluorocarbons are easily trapped in blood filter organs, resulting in depatomergaly and splenomegaly over a period of some weeks to months. Further, perfluorocarbons exhibit cytotoxic effects and are readily adsorbed by erythrocytes. This adsorption results in decreased cellular flexibility which could impair passage of the erythrocytes through capillary beds.

The encapsulation of hemoglobin in liposomes is another type of blood substitute which has been investigated. Liposome encapsulation of hemoglobin was first successfully used as a blood substitute about 40 years ago. At that time, hemoglobin was encapsulated in a collodion membrane. Liposome encapsulation has been successful in lowering the toxicity of biological agents and increasing their circulation time. Cholesterol, phosphatidylcholine and other lipids have been used to produce encapsulated hemoglobin capsules having diameters on the order of 200 to 500 microns.

Liposome encapsulated hemoglobin appears to overcome many of the complications presented by the use of perfluorocarbons and free hemoglobin. However, some clinical complications still exist. For example, problems with reticuloendothelial uptake, platelet aggregation and suppression of the reticuloendothelial system have been experienced. As is apparent, there presently is a continuing need to provide new synthetic compositions which can function effectively as a substitute for red blood cells. The synthetic composition must be capable of providing acceptable levels of oxygen transport without causing undesirable side effects. The synthetic material should be easily stored and have a reasonable shelf-life. The blood substitute should be amenable to use in a wide variety of situations including resuscitation in field trauma following massive blood loss or blood replacement during surgery. In addition, the blood substitute should be amenable to in vitro use to perfuse organs such as hearts, livers and kidneys during transport and transplantation.

SUMMARY OF THE INVENTION

In accordance with the present invention a red blood cell surrogate is provided which can be used as a blood substitute in a wide variety of situations. The red blood cell surrogate has a nanocrystalline core which is composed of a ceramic metal or polymer material. The surface of the particle is coated with an oxygen carrier anchor material. An oxygen carrier is bound to the anchor coating and an exterior layer of lipid is provided to complete the red blood cell surrogate.

As a feature of the present invention, the oxygen carrier anchor material substantially covers the surface of the nanocrystalline particle to form a glassy film which has a threshold surface energy that is sufficient to anchor the oxygen carrier to the core particle without denaturing the oxygen carrier which is bound thereto. This allows the use of a wide variety of core particle materials regardless of their respective surface energies. The anchor materials are basic sugars and allosteric effectors.

As another feature of the present invention, hemoglobin is a preferred oxygen carrier. It was discovered that hemoglobin can be anchored to the glassy film surrounding the nanocrystalline core without being denatured. The anchored hemoglobin provides oxygen transport in the same manner as the hemoglobin found in naturally occurring red blood cells.

As a further feature of the present invention, the exterior surface of the red blood cell surrogate is coated with layer of lipid provides a red cell surrogate which more closely mimics the structure and functioning of naturally occurring red blood cells. The lipid layer is designed to mimic the outer membrane of red blood cells.

As an additional feature of the present invention, an outer layer of sugar or allosteric effector may be provided as a cover for the lipid layer. This outer layer helps to prevent coagulation activation and the resultant formation of intravascular thrombosis.

The red cell surrogates of the present invention are well-suited for use in any situation where there is a need for delivery of oxygen to tissue in vivo or in vitro. The red blood cell surrogates may be used in vivo for resuscitation in field trauma following massive blood loss or as a blood replacement for blood loss in surgery. In addition, the red blood cell surrogate may be used in patients who are incapable of producing red blood cells owing to some disease process. In vitro use of the red blood cell surrogate includes perfusion of organs such as hearts, livers and kidneys during transport and storage prior to transplantation. In addition, the red blood cell surrogates may be used in cell culture systems as an optional oxygen delivery system.

The above discussed and many other features and attendant advantages of the present invention will become better understood by reference to the following detailed description.

DETAILED DESCRIPTION OF THE PREFERRED EMBODIMENT

The red blood cell surrogates in accordance with the present invention are based on nanocrystalline core particles (diameters of less than 1,000 nm) which are coated with an oxygen carrier anchor coating. An oxygen carrier, such as hemoglobin, is bound to the oxygen carrier anchor coating. The nanocrystalline core particle with the oxygen carrier bound thereto, is then coated with an exterior layer of lipid. A final exterior coating of a sugar is then applied to cover the lipid layer. The red blood cell surrogates mimic the oxygen carrying capability of naturally occurring red blood cells and have been found useful in transporting oxygen in the same manner as red blood cells both in vitro and in vivo.

The red blood cell surrogates of the present invention are similar in some respects to the viral decoy vaccines disclosed in U.S. Pat. No. 5,178,882 which issued on Jan. 12, 1993, and is owned by the same assignee as the present application. U.S. Pat. No. 5,178,882 discloses decoy viruses made up of nanocrystalline core particles on which various viral fragments or protein coatings are attached. The core particles are coated with a surface modifying agent to promote anchoring of the viral particles without denaturization thereof. The present invention is based upon this same principal except that hemoglobin or other oxygen carrier is bound to the surface energy modifying layer (i.e., oxygen carrier anchor coating) and an exterior coating of lipid is provided. The contents of U.S. Pat. No. 5,178,882 are hereby incorporated by reference.

The nanocrystalline particles which form the core of the red blood cell surrogate are made from a wide variety of inorganic materials including metals, ionic solids or ceramics. The core material may also be polymers. The particles may range in size up to about 1000 nm. The preferred particle sizes are on the order of about 10 to 200 nm. Preferred metals include chromium, rubidium, iron, zinc, selenium, nickel, gold, silver, and platinum. Preferred ceramic materials include silicon dioxide, silicon nitride, titanium dioxide, aluminum oxide, ruthenium oxide and tin oxide. The core particles may be made from materials such as diamond, calcium hydroxide, calcium oxide, calcium acetylsalicylate, calcium ascorbate, calcium carbonate, calcium citrate, calcium cyclamate, calcium gluconate, calcium glycerophosphate, calcium hypophosphate, calcium iodate, calcium lactate, calcium oxalate, phosphate, calcium pyrophosphate, calcium D-saccharate, calcium stearate, calcium succinate, calcium sulfite, calcium tartrate and calcium phosphate compositions. Preferred polymers include polystyrene, nylon and nitrocellulose. Particles made from tin oxide, titanium dioxide, calcium oxide, calcium hydroxide, or calcium phosphate diamond are particularly preferred.

Particles made from the above materials having diameters less than 1000 nanometers are available commercially or they may be produced from progressive nucleation in solution (colloid reaction), or various physical and chemical vapor deposition processes, such as sputter deposition (Hayashi, C. *J. Vac. Sci. Technol.* A5(4), Jul./Aug. 1987, pgs. 1375–1384; Hayashi, C., *Physics Today*, Dec. 1987, pgs. 44–60; MRS Bulletin, Jan 1990, pgs. 16–47). Tin oxide having a dispersed (in $H_2O$) aggregate article size about 140 nanometers is available commercially from Vacuum Metallurgical Co. (Japan). Other commercially available particles having the desired composition and size range are available from Advanced Refractory Technologies, Inc. (Buffalo, N.Y.).

Plasma-assisted chemical vapor deposition (PACVD) is one of a number of techniques that may be used to prepare suitable microparticles. PACVD functions in relatively high atmospheric pressures (on the order of one torr and greater) and is useful in generating particles having diameters of up to 1000 nanometers. For example, aluminum nitride particles having diameters of less than 1000 nanometers can be synthesized by PACVD using $Al(CH_3)_3$ and $NH_3$ as reactants. The PACVD system typically includes a horizontally mounted quartz tube with associated pumping and gas feed systems. A susceptor is located at the center of the quartz tube and heated using a 60 Khz radio frequency source. The synthesized aluminum nitride particles are collected on the walls of the quartz tube. Nitrogen gas is used as the carrier of the $Al(CH_3)_3$. The ratio of $Al(CH_3)_3$: $NH_3$ in the reaction chamber is controlled by varying the flow rates of the $N_2Al(CH_3)_3$ and $NH_3$ gas into the chamber. A constant pressure in the reaction chamber of 10 torr is generally maintained to provide deposition and formation of the ultrafine nanocrystalline aluminum nitride particles. PACVD may be used to prepare a variety of other suitable nanocrystalline particles.

Nanocrystalline Calcium hydroxide may be prepared by streaming 50 ml volumes of 0.75M of Calcium chloride and 1.5N Sodium hydroxide against each other over 10 ml of 100 mM sodium citrate during 400 W sonication in a cup horn for 15 minutes [4° C.]. The resultant white opaque solid is washed 2 times with HPLC grade sterile water and sonicated at 450 W [4° C.] for an additional hour and adjusted to 150 mg/ml to provide a dispersion of nanocrystalline particles which may be coated as described below.

In order to attach hemoglobin or other oxygen carrier to the core particle, it must first be coated with a substance that provides a threshold surface energy to the particle which is sufficient to bind the hemoglobin without denaturing it. The core particles are preferably coated by suspending them in a solution containing the dispersed surface modifying agent. It is necessary that the coating make the surface of the particle more amenable for attachment of hemoglobin or other oxygen carrier. Suitable coating substances in accordance with the present invention are basic sugars including cellobiose, trehalose, isomaltose, nystose sorbitol, lactitol, maltose and sucrose. In addition, allosteric effectors such as pyridoxal-5-phosphate; 2,3-phosphoglycerate, and sodium citrate may be used. If desired, the surface modifying coating (i.e., oxygen carrier anchor coating) can be made from a combination of basic sugars and allosteric effectors. It is only necessary that the coating provide the surface of the nanocrystalline particle with a threshold energy which is sufficient to bind hemoglobin or other oxygen carrier without denaturing the relevant oxygen transport sites.

Sugars which exhibit the molecular stabilization required in accordance with the present invention are polyhydroxylic in nature and have a relatively low molecular weight which affords them maximum rotation freedom in the glassy state. Accordingly, it is expected that low molecular weight molecules including disaccharides and related alcohols rich in hydroxy groups will afford the energetics that are classically associated with water and yet be of sufficiently small molecular weight to produce functional glasses which provide the molecular stabilization required in accordance with the present invention.

The coating solution into which the core particles are suspended contains, for example, from 1 to 30 weight/volume percent of the coating material. The solute is preferably double distilled water (ddH$_2$O). The amount of core particles suspended within the coating solution will vary depending upon the type of particle and its size. Typically, solutions with particle densities of about 100 mg/ml or greater are suitable for synthesis of the red blood cell surrogates.

The core particles are maintained in dispersion in the coating solution for a sufficient time to provide uniform coating of the particles. Sonication is the preferred method for maintaining the dispersion. Dispersion times ranging from 30 minutes to a few hours at room temperature are usually sufficient to provide a suitable coating to the particles. The thickness of the coating is preferably less than 5 nanometers. Thicknesses of the coating may vary provided that the final core particles include a uniform oxygen carrier anchor coating over substantially all of the particle surface.

The previously described calcium hydroxide nanocrystalline particles may be coated with sodium citrate as follows: 50 ml of 100 mM sodium citrate is added to 50 ml of the freshly sonicated calcium hydroxide nanocrystalline particle dispersion (150 mg/ml) and lyophilized overnight under low heat. The next morning the solid is rehydrated to 50 ml, sonicated at 450 W for 5 minutes, and washed three times with HPLC grade water. The preparation adjusted to 300 mg/ml for further hemoglobin carrier synthesis as described below.

Another exemplary coating procedure for calcium hydroxide nanocrystalline particles is as follows: 10 ml of 500 mM cellobiose is added to 50 ml of the freshly sonicated calcium hydroxide nanocrystalline particle dispersion (150 mg/ml) and lyophilized overnight under low heat. The next morning the solid is rehydrated to 50 ml, sonicated at 450 W for 5 minutes, and washed three times with HPLC grade water. The preparation is adjusted to 300 mg/ml for further hemoglobin carrier synthesis as described below.

A further exemplary coating procedure for calcium hydroxide nanocrystalline particles is as follows: 10 ml of 100 mg/ml pyridoxal-5-phosphate is added to 50 ml of the freshly sonicated calcium hydroxide nanocrystalline particle dispersion (150 mg/ml) and lyophilized overnight under low heat. The next morning the solid is rehydrated to 50 ml, sonicated at 450 W for 5 minutes, and washed three times with HPLC grade water. The preparation is adjusted to 300 mg/ml for further hemoglobin carrier synthesis as described below.

The oxygen carrier which is attached to the coated nanocrystalline core particle is preferably hemoglobin. The hemoglobin may be derived from numerous sources including human, bovine, or ovine. Purified hemoglobin is available commercially from many different sources. In addition, any of the well known techniques for isolating and purifying hemoglobin from blood may be used. Hemoglobin is the preferred oxygen carrier; however, other oxygen carrying macromolecules may be utilized if desired. Hemoglobin may be produce through recombinant engineering techniques or transgenic animals such as swine.

The hemoglobin may be attached to the coated nanocrystalline core particles by a wide variety of procedures. Preferably, a solution of purified hemoglobin is added to a solution of coated nanocrystalline core particles and agitated for a sufficient time to allow binding of the hemoglobin to the coated particles. Although it is preferred that the binding of hemoglobin to the coated core particles occur in solution, many other techniques may be used provided that intimate contact between the purified hemoglobin and the coated core particle is provided.

The amount of hemoglobin which is bound to the coated nanocrystalline particle may vary widely depending upon the intended use for the red blood cell surrogate. It is preferred that the amount of hemoglobin bound to each nanocrystalline particle be maximized as much as possible without adversely affecting the oxygen transport properties of the surrogate. When maximum oxygen transport is desired, then maximum binding of hemoglobin to the nanocrystalline particle is desired. However, when lesser degrees of hemoglobin bound to the coated nanocrystalline particles may be reduced. Preferably, an excess of hemoglobin is combined with the coated nanocrystalline particles to assure maximum hemoglobin binding.

The next step in forming the red blood surrogate of the present invention involves coating the nanocrystalline particles with a lipid. The lipids used to coat the nanocrystalline particle and bound hemoglobin are the same lipids commonly used to form liposomes. Suitable lipids include phospholipids such as phosphatidylcholine, cholesterol and phosphatidylserine. The lipid layer is applied to the nanocrystalline core particle and bound hemoglobin in the same manner as the anchor coating and hemoglobin.

It is not clear whether the core particle and bound hemoglobin need to be totally covered with a lipid layer. Preferably, the amount of lipid used to coat the core particles and bound hemoglobin will be an excess to ensure complete interaction and coating of the particles.

The final step in forming the red blood cell surrogates of the present invention involves coating the lipid layer with an outer coating. The outer coating may be made from the same sugars and allosteric effectors which are used to form the anchor coating. The outer coating is preferably applied by lyophilization of the particles in the presence of the sugar or allosteric effector. Cellobiose is a preferred outer coating. The outer coating may also be applied using any of the conventional coating processes. Preferably, the outer coating will cover substantially the entire surface of the red blood cell surrogate. This outer coating preferably will have a thickness on the order of a few nanometers. This outer stabilizing layer is designed to prevent activation of blood coagulation mechanisms in vivo and thereby reduce the possibility of intravascular thrombosis.

The red blood cell surrogates in accordance with present invention may be stored in a variety of forms. Preferably, the red blood cell surrogates are freeze dried and stored in a dry form. However, if desired, the red cell surrogate may be stored in the form of a solution. The red blood cell surrogates may be used alone or in combination with any number of other blood substitutes. When in a freeze-dried form, the red blood cell surrogates may be reconstituted with any of the well known aqueous pharmaceutical carriers. These pharmaceutical carriers include buffered saline, with or without allosteric effectors, plasma and whole blood. Solutions composed of phosphate buffered saline (PBS) and albumin are preferred carriers.

The red blood cell surrogates may be injected in vivo as concentrated or dilute suspension. Use of the red blood cell surrogate in vitro will also range from direct addition of a freeze-dried surrogate to the addition of concentrated or dilute surrogate suspensions. In general, the red blood cell surrogates of the present may be used in the same manner as naturally occurring red blood cells. Further, the red blood cell surrogates may also be used in the same manner as other synthetic blood substitutes. Examples of practice are as follows:

EXAMPLE 1

The following example demonstrates the preparation of a red blood cell surrogate in accordance with the present invention. The fabrication process involved coating ultrafine nanocrystalline diamond particles with a glassy film of disaccharides and then physically adsorbing purified hemoglobin. The assembly was then encapsulated within simple liposomes.

One (1.00) g. of acid cleaned commercial ultrafine synthetic diamond particles (GE Series 300, Worthington, Ohio) was dispersed in 5.0 ml of 100 mM cellobiose (Sigma) solution with 175 watt sonication (Branson) for 10 minutes. The colloid was then incubated at 4.0° C. overnight in a 10 kD stir cell. The following day, this colloid was lyophilized for 24 hours and reconstituted in 1.0 ml of ddH$_2$O. Unabsorbed cellobiose was removed by 10 kD stir cell ultra filtration (UF) (Filtron) against 100 ml of 20 mM phosphate buffer (pH 7.4) (PRB) and corrected to 2.0 ml. (UF) (Filtron) against 100 ml of 20 mM phosphate buffer (pH 7.4) (PRB) and corrected to 2.0 ml.

Five hundred (500) mg of human hemoglobin type A$_o$ (Sigma) was dissolved in 5.0 ml PBS (pH 6.8) (Gibco) and then ultrafiltered against 150 ml PRB at 4.0 C. in a 50 kD stir with 30 psi N2. The filtrate was adjusted to 3.0 ml. The surface modified diamond dispersion (2.0 mL) was then added to the 50 kD ultrafiltrate cell and allowed to incubate overnight with slow stirring (5 psi N$_2$). The filtrate was adjusted to 3.0 ml. The surface modified diamond dispersion (2.0 mL) was then added to the 50 kD ultrafiltrate cell and allowed to incubate overnight with slow stirring (5 psi N2, 4.0° C.). The next morning, 35 uL of phosphatidyl dipalmitoyl serine (10 mM of 6.0 mM NaOH) (Sigma), 50 uL of phosphatidyl dipalmitoyl choline [6.8 mM stock] Sigma, and 8.7 uL of cholesterol [3.9 mM stock] (Sigma) was stirred in and incubated for approximately 6.0 hours. The final product was again filtered in a 50 kD ultrafiltration cell over 30 psi N$_2$ against 20 ml PBS (pH 7.4, 4.0° C. and adjusted to 5.0 ml for an estimated hemoglobin concentration of 10 g/dL.

EXAMPLE 2

In this example, red blood cell surrogates were made in the same manner as Example 1 except that pyridoxal-5-phosphate is substituted for cellobiose as the oxygen carrier anchor coating.

50 mg of acid cleaned commercial ultrafine synthetic diamond particles (GE Series 30, Worthington, Ohio) was dispersed by 175 watt sonication (Branson) for 10 minutes, mixed with 75.0 mg of pyridoxal-5-phosphate [Sigma] and adjusted to 10.0 ml with deionized water. The mixture was spun lyophilized overnight, washed with 4–10 ml aliquots of deionized water and reconstituted to 25 mg/ml in pH 7.40, 20 mM phosphate buffer.

4.0 ml [25 mg/ml] of nanocrystalline core particles were added to 1.0 ml recovered red blood lysate hemoglobin [26.10 g/dL]. The mixture was then slowly dialyzed into 100 ml of 0.5X PRB overnight at 4.0 C. under a nitrogen head of 20 psi and through a 10 kD ultrafiltration cell. The next morning, 34 uL of phosphatidyl serine [10 mM of 6.0 mM NaOH] (Sigma), 50 uL of cholesterol [3.9 mM stock] (Sigma) was stirred in an incubated for approximately 6.0 hours. The final product was again filtered to remove free hemoglobin in a 50 kD ultrafiltration cell over 30 psi N$_2$ against 200 ml PBS (pH 7.4, 4.0° C.) and adjusted to 1.0–2.5 ml or an estimated hemoglobin concentration of 10 g/dL.

The preceding procedure was repeated at different pyridoxal-5-phosphate concentrations. As a result, red blood cell surrogates were prepared wherein the nanocrystalline particles were coated in solutions containing 1 mM pyridoxal-5-phosphate and 30 mM pyridoxal-5-phosphate.

The red blood cell surrogates prepared in Examples 1 and 2 were analyzed for oxygen dissociation characteristics as well as size distribution, electrophoretic mobility and retained molecular conformation. The red blood cell surrogates coated with cellobiose (Example 1) exhibited an oxygen dissociation (P50) of 26–30 mm Hg. The red blood cell surrogates having coatings of pyroxidal-5-phosphate should have oxygen dissociations (P50) 37 mm Hg. This compares well with the oxygen dissociation of whole human blood which is 31 mm Hg. In addition, hemoglobin-bound nanocrystalline particles were prepared in the same manner as Example 2 except that the coating of lipid was deleted. The oxygen-dissociation of the lipid-free hemoglobin-bound nanocrystalline particles was 12 mm Hg.

The electrophoretic mobility of the red blood cell surrogates produced in Examples 1 and 2 were measured with Doppler electrophoretic light scatter analysis (DELSA 440, Coulter Electronics, Inc., Hialeah, Fla.). The electrophoretic mobility was −1.7 um cm/Vs at a pH of 7.4 PRGB BUFFER at 25° C.

The size distribution of the red blood cell surrogates produced in Examples 1 and 2 were measured by both photon correlation spectroscopy at a 90° angle in PRB buffer at 22.5° C. (N4MD, Coulter) and by transmission microscopy (TEM, Zeiss 190). The red blood cell surrogates measured 187 nanometers plus or minus 37 nanometers by photon correlation. For electron microscopy, a 10 microliter drop of particles in solution was placed on a paraffin surface which included a carbon-stabilized FORMVAR GRID (Ted Pella, Inc., Redding, Calif.) which was floated on top of the drop. Due to the high surface charge of the TEM GRID, the red blood cell surrogates absorbed to the grid allowing excess solution to be removed by careful blotting. A similar method was then used to stain the particles with 2 % phosphotungstic acid. The stained grid was then dried and the red blood cell surrogates identified as having particle sizes in the range of 50–100 nanometers.

The conformational integrity of the red blood cell surrogates was verified by immunogold antibody affinity intensity. After being deposited on one nanometer TEM copper grids, the protein bound particles were incubated for one hour at 27° C. with polyclonal rabbit anti-human hemoglobin antibodies (Dako) and secondary goat anti-rabbit 30 nanometer gold-labeled antibodies (Zymed Laboratories, San Francisco, Calif.). The gold-labeled anti-bodies were observed to attach avidly to the hemoglobin present in the red blood cell surrogates.

EXAMPLE 3

In the following example, a red cell surrogate was prepared having a brushite core, cellobiose oxygen carrier anchor coating and hemoglobin oxygen carrier. The lipid layer was made from L-alpha-phosphatidyl choline, L-alpha-phosphatidyl serine and cholesterol. The outer coating was cellobiose.

The procedure used to prepare the red cell surrogate was as follows:

Preparing Calcium Phosphate Dihydrate (Brushite) Nanocrystalline Particles:

Reagents. 0.75M $CaCl_2$: 55.13 g $CaCl_2.2H_2O$ is dissolved with HPLC grade water to 0.500 L in a volumetric flask. Filter sterilize with 0.2 um sterile filtration unit and place in a sterile 500 ml culture medium flask. Store at room temperature.

0.25M $Na_2HPO_4$: 17.75 g of anhydrous $Na_2HPO_4$ is dissolved with HPLC grade water to 0.500 L in a volumetric flask. Filter sterilize with 0.2 um sterile filtration unit and place in a sterile 500 ml culture medium flask. Also store at room temperature.

Brushite synthesis. About a half hour before synthesis, prepare the sonicator by cooling down the cup horn. This is accomplished by adjusting the low temperature thermostat on the water condenser to 4° C. and dialing a setting of "4" on the peristatic circulator. Once the 4° C. mark is reached, prepare 50.0 ml of 0.75M $CaCl_2$ and 50.0 ml of 0.25M $Na_2H_2PO_4$ and load into 50 ml syringes. The syringes are then to be connected to a 3-way luer lock connector so that they are set in diametric opposition—allowing the remaining luer port to be free to dispel product. Once the mixing apparatus is set up, place a sterile 120 ml sonicating flask in the cup horn and slowly power up the sonicator to 100% power. Position the mixing apparatus so that the free luer port is over the sonicating flask. Expel syringe contents into the flask as rapidly and evenly as possible so as to empty each syringe roughly at the same time. Then quickly secure a polypropylene liner over the sonicating flask and let sonicate for an additional 15 minutes.

Brushite washing. Roughly divide the prep into two 50 ml blue top polypropylene tubes and pellet at 2000 rpm for 10 minutes (room temperature). Reconstitute by vortexing each pellet with sterile HPLC grade water to 50 ml (or tube capacity) and pellet at 2000 rpm for 10 minutes. Repeat this wash 3 more times and reconstitute the last pellets to 50.0 ml. Transfer the dispersion to a sterile 120 ml sonicating flask with polypropylene liner. Place the flask in a previously cooled sonicator cup horn at 1° C. Sonicate at 100% power for 60 minutes.

Coating Brushite Nanoparticles With a Cellobiose:
Incubation/Lyophilization.

1. Sonicate the brushite (aqueous dispersion) prepared as described above for 30 minutes at 25° C. at full power [175 Watts].
2. Then as quickly as possible, exchange suspending medium from water (stock) to a solution of 500 mM cellobiose using either a bench top microcentrifuge (30 seconds, full speed of 14,000 RPM) for small volumes or for larger volumes a floor models centrifuge (model 21K, in 50 ml centrifuge tubes, 8,000 RPM for a maximum of 2 minutes). Suspend the pelleted carbon with 500 mM cellobiose, sonicate to aid dispersion (approximately 5 minutes at 25° C. at full power [175 Watts]) and finally set the mixture on a rocking plate overnight in a cold room [4° C.].
3. The next day portion out the mixture into appropriately sized vessels for overnight lyophilization.
4. Leave the tubes capped with a layer of parafilm around the cap and place them in a freezer until the washing step.
5. Reconstitute the brushite/cellobiose in a suitable buffer depending on the application. Suitable buffers are low ionic strength buffered phosphate (PRB), water, or bicarbonate. Reconstitution in the buffer is accomplished by vortexing and a 5 minute sonication [175 Watts/25° C.].
6. Wash by repeated centrifugation (using either a bench top microcentrifuge [30 seconds, full speed of 14,000 RPM] for small volumes or for large volumes a floor model centrifuge [model 21K, in 50 ml centrifuge tubes, 8,000 RPM for a maximum of 2 minutes]) and resuspension into the buffer.
7. Take a concentration measurement by removing 1 ml of the suspension dehydrating it in a lyophilizer in a pre-weighed 1.7 ml Eppendorf tube, and massing.
8. Calculate the final volume necessary to bring the concentration to 1 mg/ml. Add enough buffer to bring the concentration of the brushite/cellobiose preparation to 1 mg/ml.

Final Preparation of Red Cell Surrogate:

The cellobiose coated brushite was then coated with hemoglobin as described in Example 1. The coating of lipid and outer coating of cellobiose were applied as follows:

All reagents were obtained from Sigma Biochemical (St. Louis, Mo.), unless otherwise noted. For a 100 ml brushite hemoglobin carrier synthesis, 6.60 g of egg yolk L-alpha-phosphatidyl choline, 0.660 g of bovine brain L-alpha-phosphatidyl serine, and 3.10 g of cholesterol was mixed in 132 mls of chloroform. Chloroform was removed by lyophilization using a Savant (Westbury, N.Y.) speed vac for at least 18 hours under low heat in 50 ml Corex tubes. Following immediately after lyophilization, 17 mls of a 500 mM solution of cellobiose was then added to the phospholipids and corrected to 100 mls with sterile water. The mixture was then sonicated at 4.0° C. in a AES2000 Branson (Westbury, Conn.) sonifier for one hour at approximately 400 Watts and added to a sterile 500 ml water jacketed reaction flask. The contents were then lyophilized overnight under analogous conditions.

The red cell surrogates produced as described above were tested in the same manner as Examples 1 and 2 and found to be effective as red blood cell surrogates.

EXAMPLE 4

Red cell surrogates are made in the same manner as Example 3 except that pyrodoxal-5-phosphate (P-5-P) is substituted for cellobiose as the oxygen carrier anchor coating. The coating of P-5-P is applied as follows:

Pellet 100 ml of the dispersion prepared in Example 3 so that the entire contents can be transferred to a 50 ml conical tube. Adjust the tube volume to 40.0 ml. Then transfer the contents in 10 ml aliquots to four 15 ml conical tubes. Dissolve 1000 mg of Pyroxidal-5-phosphate with 800 µl of 10N NaOH and adjust with water to 10 mls. Filter sterilize this clear yellow solution with a 0.2 µm acrodisc and add 2.5 ml aliquots to each of the previously prepared 4 brushite tubes. Vortex each tube a few seconds to make certain that the contents are well dispersed. Lyophilize overnight [approx. 16 hrs] at the low drying rate setting. The next morning resuspend in 50 ml aliquots of sterile HPLC grade water five more times. Pellet once more and transfer the pellets to four 15 ml conical tubes and adjust the final preparation volume with water to 40.0 ml.

As another option, P-5-P may also be substituted for cellobiose as the outer coating.

EXAMPLE 5

Red cell surrogates are made in the same manner as Example 3 except that citrate is substituted for cellobiose as the oxygen carrier anchor coating. The coating of citrate is applied as follows:

Brushite/Citrate. Pellet the 100 ml of the dispersion prepared in Example 3 so that entire contents can be transferred to a 50 ml conical tube. Adjust the tube volume to 40.0 ml. Then transfer the contents in 10 ml aliquots to four 15 ml conical tubes. Add 10 ml of 100 mM citrate to each of the 15 ml conicals and nutate for 30 minutes at room temperature. Lyophilize overnight [approx. 16 hrs] at the low drying rate setting. The next morning resuspend in 50 ml aliquots of sterile HPLC grade water five more times. Pellet once more and transfer the pellets to four 15 ml conical tubes and adjust the final preparation volume with water to 40.0 ml.

The above examples demonstrate that the red blood cell surrogates in accordance with the present invention are effective oxygen transport particles which may be used as a substitute for red blood cells both in vitro and in vivo.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A red cell surrogate comprising:
   a nanocrystalline core particle, said core particle having a surface;
   an oxygen carrier anchor coating located on the surface of said nanocrystalline core particle;
   an oxygen carrier bound to said oxygen carrier anchor coating;
   a layer of lipid surrounding said oxygen carrier; and
   an outer layer.

2. A red cell surrogate according to claim 1 wherein said nanocrystalline particle comprises a ceramic, metal or polymer.

3. A red cell surrogate according to claim 1 wherein said oxygen carrier anchor coating comprises a glassy film which substantially covers the surface of said nanocrystalline core particle, said glassy film having a threshold surface energy that is sufficient to anchor said oxygen carrier to said core particle without denaturing said oxygen carrier.

4. A red cell surrogate according to claim 3 wherein said glassy film comprises a sugar selected from the group of basic sugars consisting of cellobiose, trehalose, isomaltose, nystose sorbitol, lactitol, maltose and sucrose.

5. A red cell surrogate according to claim 3 wherein said glassy film comprises an allosteric effector selected from the group consisting of pyridoxal-5-phosphate, 2,3-phosphoglycerate, and sodium citrate.

6. A red cell surrogate according to claim 3 wherein said glassy film comprises a basic sugar and an allosteric modifier.

7. A red cell surrogate according to claim 1 wherein said oxygen carrier comprises hemoglobin.

8. A red cell surrogate according to claim 7 wherein said oxygen carrier comprises human hemoglobin.

9. A red cell surrogate according to claim 1 wherein said exterior layer of lipid comprises a phospholipid.

10. A red cell surrogate according to claim 9 wherein said phospholipid is selected from the group consisting of phosphatidylcholine, cholesterol and phosphatidylserine.

11. A red cell surrogate according to claim 1 wherein outer layer comprises a sugar or allosteric effector.

12. A red cell surrogate according to claim 11 wherein said outer layer sugar is selected from the group consisting of cellobiose, trehalose, isomaltose, nystose sorbitol, lactitol, maltose and sucrose.

13. A red cell surrogate according to claim 11 wherein said outer layer allosteric effector is selected from the group consisting of pyridoxal-5-phosphate, 2,3-phosphoglycerate and sodium citrate.

14. A composition of matter comprising:
   A. a red cell surrogate comprising:
      a nanocrystalline core particle, said core particle having a surface;
      an oxygen carrier anchor located on the surface of said nanocrystalline core particle;
      an oxygen carrier bound to said oxygen carrier anchor coating;
      a layer of lipid surrounding said oxygen carrier;
      an outer layer; and
   B. a physiological acceptable carrier for said red cell surrogate.

15. A method for delivering oxygen to cells, said method comprising the step of treating said cells with a red blood cell surrogate, said surrogate comprising:
   a nanocrystalline core particle, said core particle having a surface;
   an oxygen carrier anchor coating located on the surface of said nanocrystalline core particle;
   an oxygen carrier bound to said oxygen carrier anchor coating;
   a layer of lipid surrounding said oxygen carrier;
   an outer layer.

16. A method for delivering oxygen to cells according to claim 15 wherein said nanocrystalline particle comprises a ceramic, metal or polymer.

17. A method for delivering oxygen to cells according to claim 15 wherein said oxygen carrier anchor coating comprises a glassy film which substantially covers the surface of said nanocrystalline core particle, said glassy film having a threshold surface energy that is sufficient to anchor said oxygen carrier to said core particle without denaturing said oxygen carrier.

18. A method for delivering oxygen to cells according to claim 17 wherein said glassy film comprises a sugar selected from the group of basic sugars consisting of cellobiose, trehalose, isomaltose, nystose sorbitol, lactitol, maltose and sucrose.

19. A method for delivering oxygen to cells according to claim 17 wherein said glassy film comprises an allosteric effector selected from the group consisting of pyridoxal-5-phosphate, 2,3-phosphoglycerate and sodium citrate.

20. A method for delivering oxygen to cells according to claim 17 wherein said glassy film comprises a basic sugar and an allosteric modifier.

21. A method for delivering oxygen to cells according to claim 15 wherein said oxygen carrier comprises human hemoglobin.

22. A method for delivering oxygen to cells according to claim 15 wherein said exterior layer of lipid comprises a phospholipid.

23. A method for delivering oxygen to cells according to claim 15 said exterior layer of lipid comprises a phospholipid.

24. A method for delivering oxygen to cells according to claim 23 wherein said phospholipid is selected from the group consisting of phosphatidyl-choline, cholesterol and phosphatidylserine.

25. A method for delivering oxygen to cells according to claim 15 wherein said cells are located in vivo.

26. A method for delivering oxygen to cells according to claim 15 wherein said cells are located in vitro.

27. A method for delivering oxygen to cells according to claim 15 wherein said outer layer comprises a sugar or allosteric effector.

28. A method for delivering oxygen to cells according to claim 15 wherein said outer layer sugar is selected from the group consisting of cellobiose, trehalose, isomaltose, nystose sorbitol, lactitol, maltose and sucrose.

29. A method for delivering oxygen to cells according to claim 15 wherein said outer layer allosteric effector is selected from the group consisting of pyridoxal-5-phosphate, 2,3-phosphoglycerate and sodium citrate.

* * * * *